US008735122B2

(12) United States Patent
Henot et al.

(10) Patent No.: US 8,735,122 B2
(45) Date of Patent: May 27, 2014

(54) METHOD FOR THE PURIFICATION OF HEAT SHOCK PROTEINS

(75) Inventors: Frederic Henot, Brussels (BE); Thierry Legon, Bierbeek (BE); Sabine Pirotton, Brussels (BE); Gael Placier, Brussels (BE)

(73) Assignee: Biotech Tools S.A., Brussels (BE)

( * ) Notice: Subject to any disclaimer, the term of this patent is extended or adjusted under 35 U.S.C. 154(b) by 1285 days.

(21) Appl. No.: 12/311,755

(22) PCT Filed: Oct. 12, 2007

(86) PCT No.: PCT/EP2007/060875
§ 371 (c)(1),
(2), (4) Date: Jul. 24, 2009

(87) PCT Pub. No.: WO2008/043832
PCT Pub. Date: Apr. 17, 2008

(65) Prior Publication Data
US 2010/0068744 A1    Mar. 18, 2010

Related U.S. Application Data

(60) Provisional application No. 60/853,567, filed on Oct. 23, 2006.

(30) Foreign Application Priority Data

Oct. 13, 2006   (EP) .................................. 06122292

(51) Int. Cl.
*C12N 9/14*       (2006.01)
*A23J 1/00*       (2006.01)
*A61K 38/43*      (2006.01)

(52) U.S. Cl.
USPC ........... 435/195; 530/412; 530/417; 424/94.1

(58) Field of Classification Search
None
See application file for complete search history.

(56) References Cited

U.S. PATENT DOCUMENTS 6,709,672 B2 * 3/2004 Henot et al. .................. 424/439
2002/0119163 A1   8/2002 Srikumaran

FOREIGN PATENT DOCUMENTS

| JP | 2003-00056 | 1/2003 |
| WO | 00/71723 | 11/2000 |
| WO | 2005/002619 | 1/2005 |

OTHER PUBLICATIONS

McCarty et al. DnaK as a thermometer: threonine-199 is site of autophosphorylation and is critical for ATPase activity. PNAS 1991 88 (21) 9513-9517; doi:10.1073/pnas.88.21.9513.*

Bloemendal et al., "Experimental immunization with anti-rheumatic bacterial extract OM-89 induces T cell responses to heat shock protein (hsp)60 and hsp70; modulation of peripheral immunological tolerance as its possible mode of action in the treatment of rheumatoid arthritis (RA)," Clin Exp Immunol, 110:72-78 (1997).
Galdiero et al., "Modulation of costimulatory molecules CD80/CD86 on B cells and macrophages by stress proteins GroEL, GroES and DnaK," Int J Immunopathol Pharmacol., 18(4):637-644 (2005) (Abstract).
Jordan et al., "Modulation of the ATPase Activity of the Molecular Chaperone DnaK by Peptides and the DnaJ and GrpE Heat Shock Proteins," The Journal of Biological Chemistry, 270(9):4563-4569 (1995).
Schönfeld et al., "The DnaK Chaperone System of *Escherichia coli*: Quaternary Structures and Interactions of the DnaK and GrpE Components," The Journal of Biological Chemistry, 270(5): 2183-2189 (1995).
Smith et al., "Fast and accurate method for quantitating *E. coli* host-cell DNA contamination in plasmid DNA preparations," Biotechniques, 26(3): 518-526 (1999) (Abstract).
Tobian et al., "Bacterial Heat Shock Proteins Enhance Class II MHC Antigen Processing and Presentation of Chaperoned Peptides to CD4 T Cells," J Immunol, 173:5130-5137 (2004).
Tobian et al., "Bacterial Heat Shock Proteins Promote CD91-Dependent Class I MHC Cross-Presentation of Chaperoned Peptide to CD8+ T Cells by Cytosolic Mechanisms in Macrophages," J Immunol 172:5277-5286 (2004).
Van Eden et al., "Heat-shock proteins induce T-cell regulation of chronic inflammation," Nat Rev Immunol., 5 (4):318-330 (2005) (Abstract).
Eremeeva et al., "Western blotting analysis of heat shock proteins of *Rickettsiales* and other eubacteria," FEMS Microbiology Letters, vol. 167, No. 2, 1998, pp. 229-237.
Gross et al., "Control of Protein Synthesis by Hemin. Purification of a rabbit reticulocyte hsp 70 and characterization of its regulation of the activation of the hemin-controlled eIF-2($\alpha$) Kinase," Journal of Biological Chemistry, vol. 269, No. 36, Sep. 1994, pp. 22738-22748.
Grossmann et al., "Proteomics show Hsp70 does not bind peptide sequences indiscriminately in vivo," Experimental Cell Research, vol. 297, No. 1, Jul. 2004, pp. 108-117.
Hentz et al., "Bifunctional Fusion Proteins of Calmodulin and Protein A as Affinity Ligands in Protein Purification and in the Study of Protein—Protein Interactions," Analytical Chemistry, vol. 68, No. 22, Nov. 1996, pp. 3939-3944.
Hinode et al., "A general procedure for the isolation of heat-shock proteins from periodontopathogenic bacteria," Journal of Microbiological Methods, vol. 25, No. 3, 1996, pp. 349-355.
Jindal et al., "Human Stress Protein hsp70: Overexpression in *E. coli*, Purification and Characterization," Bio/Technology, vol. 13, No. 10, 1995, pp. 1105-1109.
Martinez et al., "HSP60, HSP70 and HSP90 from *Trichinella spiralis* as targets of humoral immune response in rats," vol. 87. No. 6, 2001, pp. 453-458.

(Continued)

*Primary Examiner* — Yong Pak
(74) *Attorney, Agent, or Firm* — Dardi & Herbert, PLLC; Peter S. Dardi

(57) ABSTRACT

Recombinant purified DnaK—having a ATPase activity without the addition of an other chaperone protein—essentially free of T-cell stimulating impurities.

19 Claims, 11 Drawing Sheets

(56) References Cited

OTHER PUBLICATIONS

Figure 1:
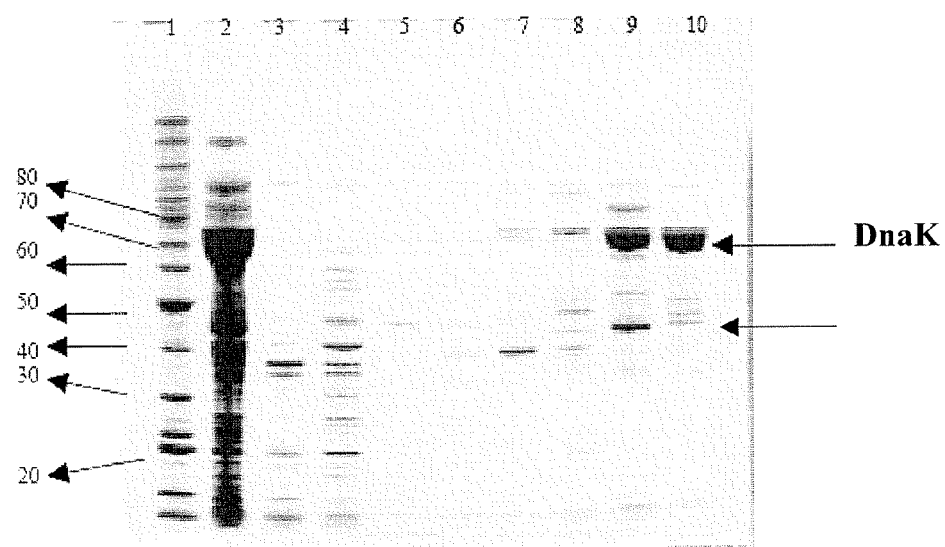

Meng et al., "Three-step purification of gp96 from human liver tumor tissues suitable for isolation of gp96-bound peptides," Journal of Immunological Methods, vol. 264, No. 1-2, 2002, pp. 29-35.

Menoret, "Purification of recombinant and endogenous HSP70s," Methods, vol. 32, No. 1, 2004, pp. 7-12.

Menoret et al., "Purification of multiple heat shock proteins from a single tumor sample," Journal of Immunological Methods, vol. 237, No. 1-2, 2000, pp. 119-130.

Nandan et al., "A rapid, single-step purification method for immunogenic methods of the hsp 70 family: validation and application," Journal of Immunological Methods, vol. 176, No. 2, 1994, pp. 255-263.

Nicoll et al., "Approaches to the isolation and characterization of molecular chaperones," Protein Expression and Purification, vol. 46, No. 1, 2006, pp. 1-15.

Peng et al., "Purification of immunogenic heat shock protein 70-peptide complexes by ADP-affinity chromatography," Journal of Immunological Methods, vol. 204, No. 1, 1997, pp. 13-21.

Sherman et al., "Heat shock of *Escherichia coli* increases binding of dnaK (the hsp70 homolog) to polypeptides by promoting its phosphorylation," Proceedings of the National Academy of Science, vol. 90, No. 18, Sep. 1993, pp. 8648-8652.

Tokunaga et al., "Purification and Characterization of BiP/Kar2 Protein from *Saccharomyces cerevisiae*," Journal of Biological Chemistry, vol. 267, No. 25, 1992, pp. 17553-17559.

Udono et al., "Hsp-antigen fusion and their use for immunization," Methods, vol. 32, No. 1, 2004, pp. 21-24.

Welch et al., "Rapid Purification of Mammalian 70,000-Dalton Stress Proteins: Affinity of the Proteins for Nucleotides," Molecular and Cellular Biology, vol. 5, No. 6, 1985, pp. 1229-1237.

Yoshimune et al., "Hsc62, a New DnaK Homologue of *Escherichia coli*," Biochemical and Biophysical Research Communications, vol. 250, No. 1, 1998, pp. 115-118.

Zylicz et al., "Purification and Properties of the *Escherichia coli* dnaK Replication Protein," Journal of Biological Chemistry, vol. 259, No. 14, 1984, pp. 8820-8825.

Galdiero, "Cytokine and Adhesion Molecule Expression in Human Monocytes and Endothelial Cells Stimulated with Bacterial Heat Shock Proteins", Infection and Immunity, 65(2):699-707 (Feb. 1997).

Marcatili et al., TNF-$\alpha$, IL-1$\alpha$, IL-6 and ICAM-1 expression in human keratinocytes stimulated in vitro with *Escherichia coli* heat-shock proteins, Microbiology, 143:45-53 (1997).

Skowyra et al., "The *E. coli* dnaK Gene Product, the hsp70 Homolog, Can Reactivate Heat-Inactivated RNA Polymerase in ATP Hydrolysis-Dependent Manner," Cell 62(5): 939-944 (Sep. 7, 1990).

Translation of Office Action for corresponding Japanese Patent Application No. 2009-531855, mailed Oct. 2, 2012.

* cited by examiner

Lane 1: BenchMark protein ladder
Lane 2: Filtered cell lysate
Lane 3: Elution fractions F26-27
Lane 4: Elution fractions F29-33
Lane 5: Elution fractions F34-38
Lane 6: Elution fractions F41-46
Lane 7: Elution fractions F49-52
Lane 8: Elution fractions F53-57
Lane 9: Elution fractions F65-70
Lane 10: Elution fractions F71-77

Lane 2: BenchMark protein ladder
Lane 3: Load
Lane 4: Flow Through
Lane 5: Elution fractions 1-9
Lane 6: Elution fractions 18-27
Lane 7: Elution fractions 28-41
Lane 8: Elution fractions 42-48

Lane 1: BenchMark protein ladder
Lane 2: Permeate of the diafiltration on 30 kDa membrane
Lane 3: Retentate of the diafiltration on 30 kDa membrane
Lane 4: Sample after chromatography on Sephacryl S100 HR resin Lane 1: 10 kDa molecular weight ladder
Lane 2: DnaK preparation after QSHP + HA
Lane 3: DnaK preparation after QSHP + HA + GS
Lane 4: DnaK preparation after QSHP + GS lane 1 : molecular weight markers
lane 2 : 10 µg DnaK
lane 3 : 5 µg DnaK
lane 4 : 1 µg DnaK
lane 5 : 0.2 µg DnaK
lane 6 : 0.1 µg DnaK
lane 7 : 0.05 µg DnaK
lane 8 : 0.025 µg DnaK
lane 9 : 0.01 µg DnaK

METHOD FOR THE PURIFICATION OF HEAT SHOCK PROTEINS

RELATED APPLICATION

This application is a national stage filing of PCT Application No. PCT/EP2007/060875 filed Oct. 12, 2007, which claims priority to European Patent Application No. 06122292.3 filed Oct. 13, 2006 and U.S. Provisional Application No. 60/853,567 filed Oct. 23, 2006, each of which are hereby incorporated herein by reference.

TECHNICAL FIELD OF THE INVENTION

The present invention relates to a method for the purification of Heat Shock Proteins.

INTRODUCTION TO THE INVENTION

The expression of Heat Shock Proteins (HSPs) can be upregulated by all cells under conditions of stress. They are molecular chaperones and are involved in protein folding.

HSPs are classified in about six families and highly conserved throughout evolution.

Complexes between HSPs and peptides play a role in antigen presentation. HSPs are also involved in some autoimmune diseases. For a review, see van Eden et al., Nature Reviews. Immunology 5 (2005) 318-330.

DESCRIPTION OF THE INVENTION

DnaK is the bacterial member of the family HSP 70. Methods for the purification of DnaK are known, but the purity of the preparations is questionable. Typically, DnaK preparations are considered pure, if only one band is detectable in SDS-PAGE. Nevertheless, such preparations are not very pure.

Schönfeld et al. J. Biol. Chem. 270 (1995) 2183-2189 describe an SDS-PAGE pure DnaK, but the gel filtration analysis shows at least three peaks.

Methods for purification of HSP are known, see for example
  Nandan et al. J., Immunological Methods (1994) 176: 255-264,
  Grossmann et al., Exp. cell Res. (2004) 297: 108-117,
  Peng et al., J. Immunological Methods (1997) 204: 13-21 and
  Jindal et al., Biotechnology (1995) 13: 1105-1109.

Inconsistent data have been reported in the past regarding the immunological properties of HSP, especially DnaK. DnaK enhances the processing of antigens through the Major Hiscompatibility Complex (MHC) of class I or class II on antigen presenting cells (Tobian et al., J. Immunological 172 (2004), 5277-5286; Tobian, Canaday, Harding J. Immunol. 173 (2004) 5130-5137). Native DnaK, depending on their origin, the dosage and the route of administration, can display different, even contradictory, types of immunological effects (van Eden, van der Zee and Prakken Nat Rev. Immunol. 5 (2005): 318-330). Autoimmune responses against autologous HSP have been observed in chronic inflammatory diseases, such as rheumatoid arthritis, type I diabetes and atherosclerosis. Antigenic cross-reaction between bacterial HSP and autologous HSP are suspected to be the cause of autoimmunity development. On the other hand, in clinical trials in type I diabetes and rheumatoid arthritis, HSP have also been shown to promote a switch from a pro-inflammatory cytokine-secretion profile T cell to a regulatory cytokine secretion profile, suggesting an immunoregulation of the inflammatory disease (Bloemendal et al., Clin. Exp. Immunol. 110 (1997): 72-78). More recently, Galdiero et al. have reported that DnaK does not induce the increase of expression of costimulatory molecules (CD80/CD86) on lymphocytes and macrophages (Galdiero et al., Int. J. Immunopathol. Pharmacol. 18 (2005) 637-644).

It is believed that these inconsistencies are based on different purification methods yielding DnaK in combination with various impurities and contaminants. Moreover, since DnaK is an ATPase, it binds adenine nucleotides. Different forms of DnaK coexist and can be purified: DnaK loaded with ATP, DnaK loaded with ADP and DnaK free of nucleotides. These different forms of DnaK could have different immunological effects.

It is the object of the present invention to provide a method for the purification of DnaK overcoming at least some of the drawbacks of prior art, especially providing DnaK of increased purity.

The problem is solved in one aspect by a recombinant purified heat shock protein HSP, preferably DnaK
  having an ATPase activity without the addition of any other chaperone protein
  free of T-cell stimulating impurities.

The purified recombinant heat shock protein is characterized by its ATPase activity without the addition of any other chaperone protein. A suitable test method for ATPase activity is described in the examples.

Furthermore, the preparation is free of T-cell stimulating impurities. This requires a very low endotoxin content. The preparation does not show an effect on TH-1 (production of interferon-γ) and TH-2 (IL-5 or IL-13 production). This is further described in the examples.

The preparation is preferably free of immuno-stimulating impurities, including T-cell-stimulating impurities.

"Essentially free of immunostimulating impurities" means:
  no T-cell proliferation is observed up to 30 µg/ml
  no TNF-α production is observed up to 10 µg/ml.

A further object of the invention is a DnaK having:
a) a purity of 95% by weight or more
b) a residual DNA contamination≤1 ng/mg of protein
c) a residual host cell protein contamination (HCP)≤5% by weight
d) an endotoxin contamination<0.5 E.U./µg of protein.

The purity of the purified DnaK is calculated on a "weight per protein" basis, i.e. at least 95% of all proteins are DnaK. Preferably the content is at least 97%, more preferably at least 98% by weight of protein.

Preferably this value is determined by analysing of an SDS-PAGE gel followed by coomassie staining and densitometry.

The content of DNA is preferably very low, i.e. ≤1 ng/mg of protein, preferably ≤0.5 ng/mg of protein. The DNA contamination is measured using RT-PCR using specific primers.

The test condition depends on the type of expression system. For example for expression in *E. coil.*, specific primers for 23S DNA are suitable. For *P. pasteuris,* suitable primers are selected in the 18S DNA. These method are known to a person skilled in the art.

Furthermore, the residual host cell protein contamination is <5% by weight, preferably <1% by weight, more preferably ≤0.0001% by weight. Preferably this is determined in an ELISA test, commercially available from Cygnus Technologies Inc., USA, under the product name "Kit *E. coli* host cell proteins", for measuring *E. coil* cell proteins. The test system must be selected corresponding to the expression system, i.e.

Cygnus Technologies Inc. has also developed corresponding ELISA for other expression systems. As an alternative other methods such as SDS-PAGE with silver staining, HPLC or Western Blotting are suitable.

The endotoxin contamination is <0.5 E.U./μg of protein as shown by LAL kinetic test, commercially available from Cambrex Corporation, USA, under the product name "Kinetic-QCL®. Preferably the content is <0.1 E.U./μg of protein and preferably <0.01 E.U./μg of protein.

It has now been understood that DnaK may have contaminations with immunostimulating impurities, especially
proteins,
peptides,
nucleic acid,
lipopolysaccharides (LPS).

DnaK is a chaperone protein and, therefore, binds to other proteins and peptides.

Purification methods of prior art were obviously not able to remove both, bound and unbound impurities in DnaK preparations. Surprisingly, the purification procedure of the invention makes it possible to obtain a highly pure recombinant DnaK, essentially free of immunostimulating impurities.

For use in pharmaceutical preparations, especially as an adjuvant, it is absolutely necessary that the DnaK does not contain immunostimulating impurities.

A further aspect of the invention is a method for the purification of a recombinant heat shock protein, preferably DnaK from a cell lysate comprising the steps of
a) ion exchange chromatography
b) hydroxylapatite chromatography
c) gelatin chromatography.

In a preferred aspect of the invention, the DnaK is from saprophytic bacteria such as *E. coli* or pathogenic bacteria, such as *Mycobacterium tuberculosis*.

In a preferred embodiment, the ion exchange chromatography is an anion exchange chromatography.

For the hydroxylapatite chromatography, a hydroxylapatite type II chromatography is preferred.

In one embodiment, the gelatin chromatography is conducted on gelatin sepharose. The DnaK is preferably desorbed from the gelatin using a nucleotide, e.g. ADP, ATP.

A further aspect of the invention is a method for forming a complex between recombinant DnaK and at least one peptide or at least one protein comprising the steps of
a) combining recombinant DnaK of the invention with ATP at a molar ratio DnaK:ATP of 1:1 to 1:10;
b) adding at least one peptide or at least one protein;
c) incubating at a temperature of 10° C. to 60° C., preferably 20° C. to 45° C.

A further aspect is a mixture or complex between recombinant purified DnaK of the invention and at least one peptide or at least one protein. Preferably proteins are used in a denaturated form.

The present invention also covers combinations of DnaK with two or more different peptides or the combination of DnaK with several (optionally denaturated) proteins and complexes between DnaK and peptides and (optionally denaturated) proteins.

Suitable peptides are for example insulin, thyroglobulin, thyroid peroxidase, type II collagen, gliadin, GAD65, proteolipid protein, S-antigen, acetylcholin receptor, haptenized colonic proteins, interphotoreceptor retinoid binding protein, myelin basic protein, myelin oligodendrocyte glycoprotein, peripheral nerve P2, cytoplasmic TSH receptor, intrinsic factor, lens proteins, platelets, nucleoproteins such as histones, heat shock proteins, MHC I, MHC II, MHC-peptides complexes, milk allergens, venom allergens, egg allergens, weed allergens, grass allergens, tree allergens, shrub allergens, flower allergens, grain allergens, fungi allergens, fruit allergens, berry allergens, nut allergens, seed allergens, bean allergens fish allergens, shellfish allergens, meat allergens, spices allergens, insect allergens, mite allergens, animal allergens, animal dander allergens, allergens of Hevea brasiliensis, coagulation factors and blood group antigens, vegetables allergens, mould allergens, cytokines, proteins or peptides involved in neurodegenerative diseases (for example Alzheimer), peptides loaded with addiction substances and fragments thereof. These proteins could be used either directly, preferably in a denaturated form or after hydrolysis into smaller fragments.

A further aspect of the invention is the use of the DnaK of the invention in a pharmaceutical composition as a carrier protein, or as an adjuvant inducing an humoral response, a regulatory T-cell response in the absence of any other T-cell response.

A further aspect is the use of the DnaK of the invention or the mixture of the invention or the complex of the invention for in-vivo and/or in-vitro diagnostics and the use of the recombinant purified DnaK of the invention or the complex of the invention for the preparation of a pharmaceutical composition for inducing the tolerance, wherein the tolerance is suitable in the treatment and/or prevention of allergy, autoimmune disease or graft rejection, or neurodegenerative diseases.

In all kinds of application the DnaK of the invention may be used either in complex with ATP, in complex with ADP or free of nucleotides. For some uses it is also useful to hydrolyze the DnaK of the invention. "Free of nucleotides" is understood as less than 5% nucleotide on a molar basis.

Typical autoimmune diseases are inter alias Systemic Lupus erytematosus disease, Sjögren's disease, rheumatoid polyarthritis, as well as pathologies such as sarcoidosis and osteopenia, spondylarthritis, scleroderma, multiple sclerosis, amyotrophic lateral sclerosis, hyperthyroidism, Addison's disease, autoimmune hemolytic anemia, Crohn's disease, Goodpasture's syndrome, Graves' disease, Hashimoto's thyroiditis, idiopathic purpural hemorrhage, insulin-dependent diabetes, myasthenia, pemphigus vulgaris, pernicious anemia, poststreptococcal glomerulonephritis, psoriasis and spontaneous sterility.

The medicament may be administered for example intraveneously, intramusculary, orally, intranasally or intrapulmonary. Preferred ways are sublingual, buccal or entric delivery.

"Sublingual administration" and "buccal administration" are methods wherein the substance is combined in a pharmaceutical formulation which allows absorption of at least one substance in the mouth mucosa. Sublingual administration involves the patients holding a (sublingual) pharmaceutical composition or dosage from under their tongue while the substance diffuses into the mouth, through the mucosa lining the mouth. In buccal administration, the patients hold the (buckle) pharmaceutical composition or dosage from between their cheek and gingiva (gum) instead of under the tongue. The buccal administration can be chewed to allow faster buccal absorption or release; the present invention therefore provides in a preferred embodiment a gum-based formulation or a chewing gum formulation.

"Enteric delivery" is a method wherein the substance is in a pharmaceutical formulation which protects the active ingredient from absorption and/or degradation prior to entry into the intestine. Preferably absorption is effected in the ileum, duodenum or jejunum. In one preferred embodiment, the said pharmaceutical formulation can be a suppository.

Especially suitable formulation includes coating with polymers, e.g. as sold under the trademark Eudragit®, commercially available from Degussa, Germany, or cellulose acetophthalate available from Fagron or hydroxypropyl methylcellulose phthalate available from Shin-Etsu Chemicals Co., Ltd. These polymers are suitable for solid oral formulations which are released in the intestine. In a preferred embodiment, suitable pharmaceutical formulations are comprising any needed binders or excipients for the neutralization of hydrochloric acid (gastric acid secretion) and/or the inhibition of pepsin and/or the stimulation of bicarbonate and mucus secretion in a patient.

Neutralization of hydrochloric acid and/or inhibition of pepsin in the stomach can be achieved for example with sucralfate or a proton-binding polymer, such as but not limited to polyethylenimine, or any neutralizing anti-acid (ant-acid) or any acid blocker selected from the group consisting of aluminum salts, bismuth salts, magnesium salts, sodium bicarbonate, potassium bicarbonate, potassium citrate, sodium potassium tartrate, tricalcium phosphate, and mixtures thereof.

Some other types of acid blockers that can be used in the suitable formulation are called gastric proton pump inhibitors (or gastric H+/K+ ATPase inhibitors), prostaglandin analogues and histamine H2-receptor antagonists. These include, but are not limited to, misoprostol, ranitidine (used in ZAN-TAC®), cimetidine (used in TAGAMET®), nizatidine (used in AXID®), famotindine (used in PEPCID®), sufotidine, roxatidine, bisfentidine, tiotidine, lamtidine, niperotidine, mifentidine, zaltindine, loxtidine, omeprazole (used in PRIS-OLEC®), and rabeprazole.

Preferably, the DnaK is used with bulking agents selected from non-reducing sugars.

In another preferred embodiment, the suitable formulation comprises a microsphere of the said at least one substance bound to or encapsulated in an inert particle in whatever shape or form, having a mesh size of about 30-35 mesh (about 600 μm to 500 μm) or greater than about 40 mesh, and most preferably in the range of about 45 to 200 mesh, and may be for example a nonpareil, a silica powder, a salt crystal or a sugar crystal.

LEGENDS OF THE FIGURES

FIG. 1: SDS-PAGE analysis after Q-sepharose HP chromatography in accordance with example 1.

Figure 2:
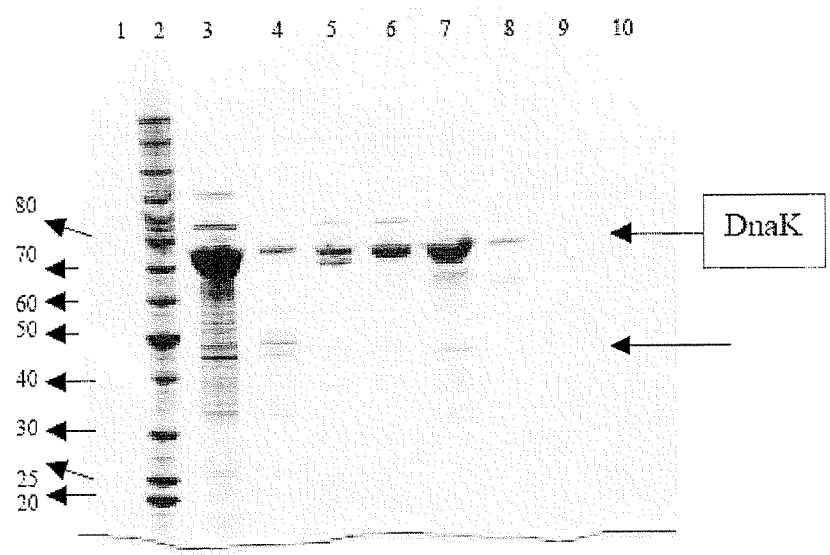

FIG. 2: SDS-PAGE analysis after hydroxyapatite type II chromatography in accordance with example 1.

Figure 3:
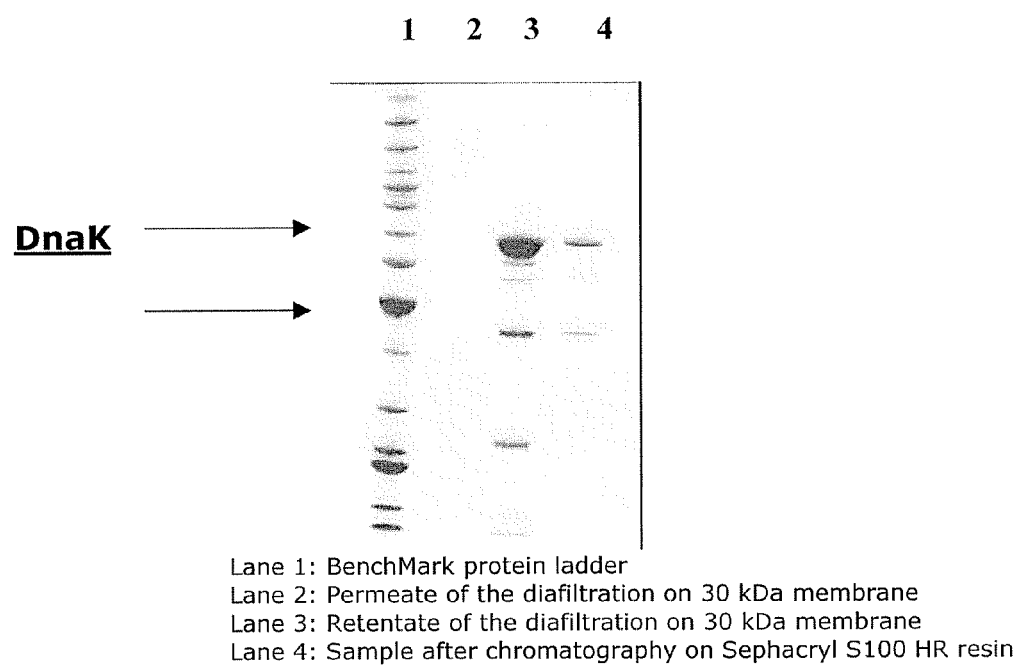

FIG. 3: SDS-PAGE analysis after diafiltration/size exclusive chromatography.

Figure 4:
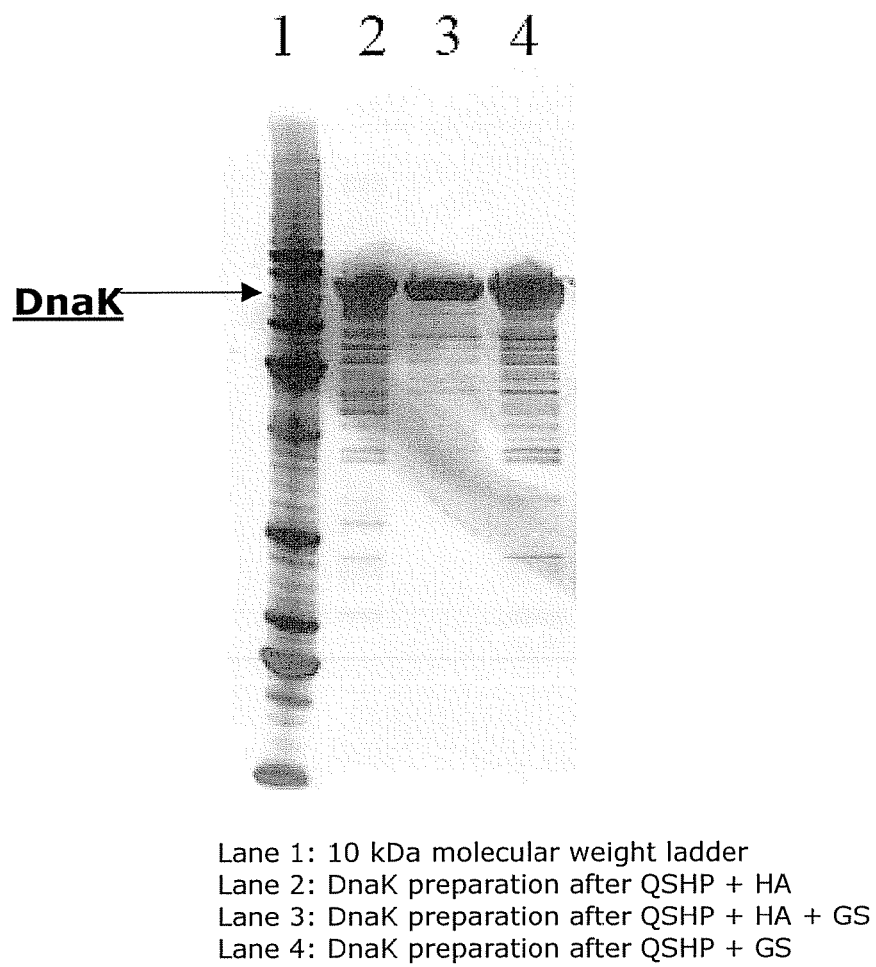

FIG. 4: SDS-PAGE analysis after gelatin sepharose chromatography. Samples (5 μg of each preparation) were denaturated and loaded on a 12% Bis/Tris NU-PAGE gel. After electrophoresis, the proteins were stained by Silver staining. QSHP=Q Sepharose HP; HA=Hydroxyapatite; GS=Gelatin Sepharose.

Figure 5:
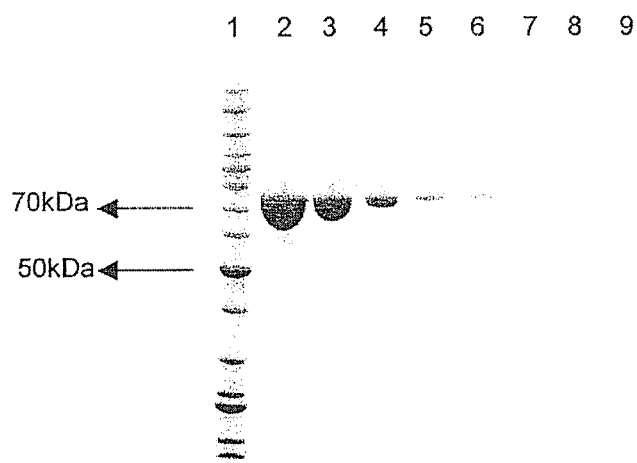

FIG. 5: SDS-PAGE analysis of the purified DnaK. The drug substance is denaturated and loaded on a 4-12% Bis/Tris NU-PAGE gel. Following electrophoresis, the protein was stained with Coomassie blue R250.

Figure 6:
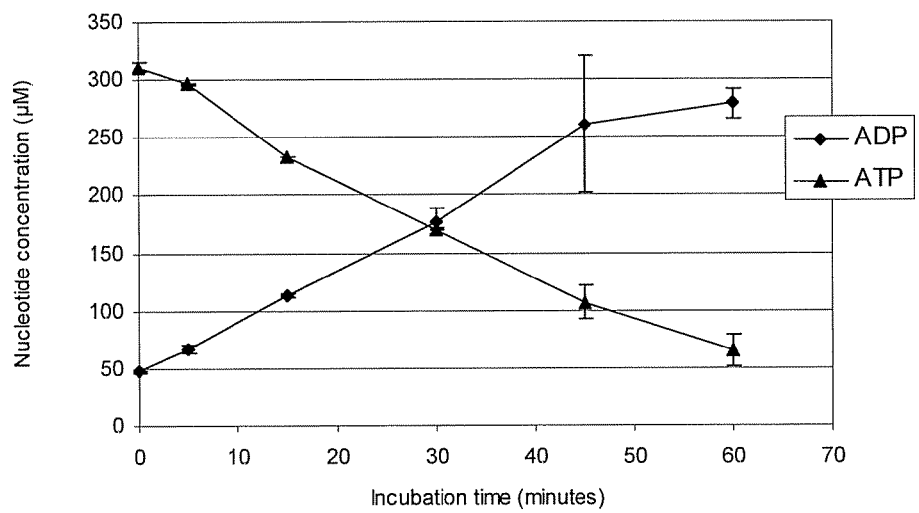

FIG. 6: ATPase activity of DnaK.

Figure 7:
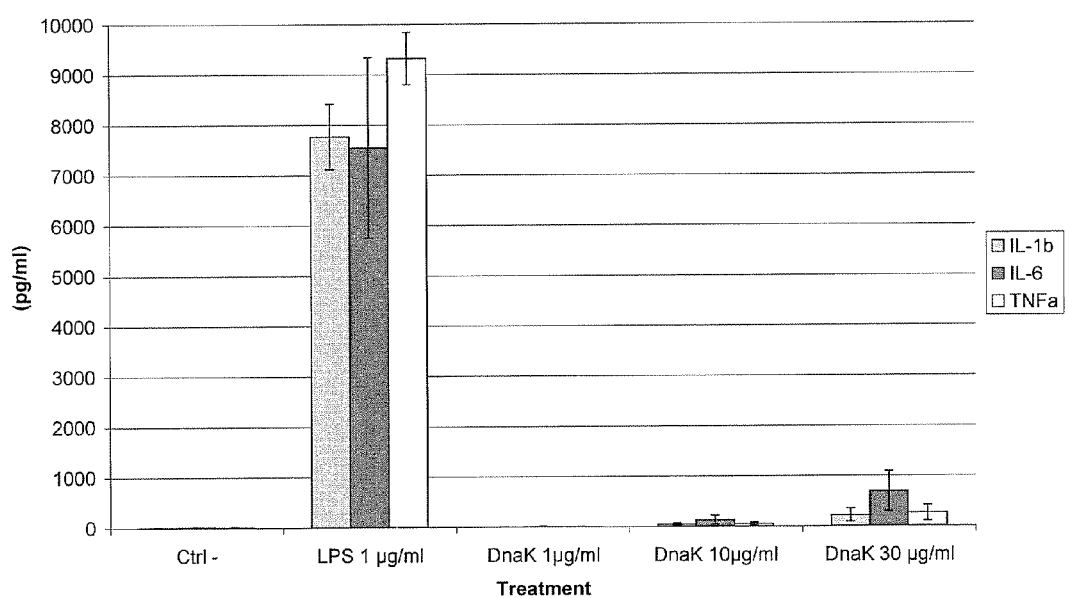

FIG. 7: Pro-inflammatory effect of DnaK. Whole blood was incubated in the presence of different concentrations of DnaK or bacterial lipopolysaccharides (LPS). The cytokines interleukin-1b (IL-1b), interleukin-6 (IL-6) and Tumour Necrosis Factor-α (TNFα) were quantitated by ELISA.

Figure 8:
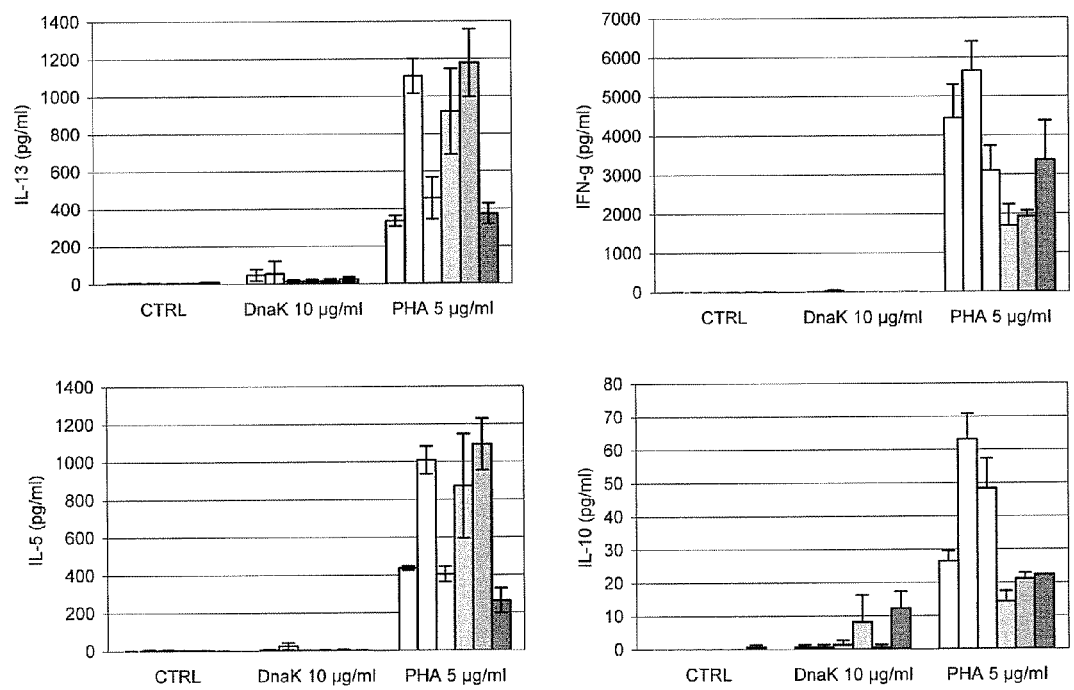

FIG. 8: Effect of the DnaK on T-cell responses. Human PBMC were incubated 6 days in the presence of DnaK (10 μg/ml) or phytohemagglutinin (5 μg/ml). The different cytokines were quantitated in the culture medium, by ELISA. Results are expressed as mean±deviation of 2 determinations, for 6 different donnors. CTRL=control.

Figure 9:
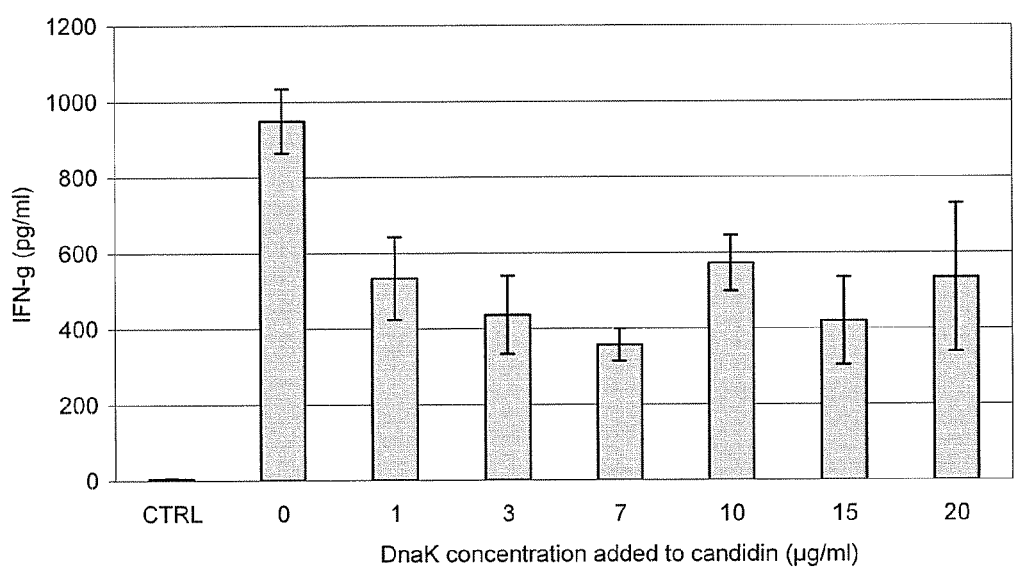

FIG. 9: Effect of DnaK on IFN-γ production induced by candidin. Human PBMC were incubated 3 days in the presence of candidin (3.5 μg/ml) and increasing concentrations of DnaK. IFN-γ production was quantitated by ELISA in the culture medium. Results are expressed as mean±standard deviation of 4 determinations.

Figure 10:
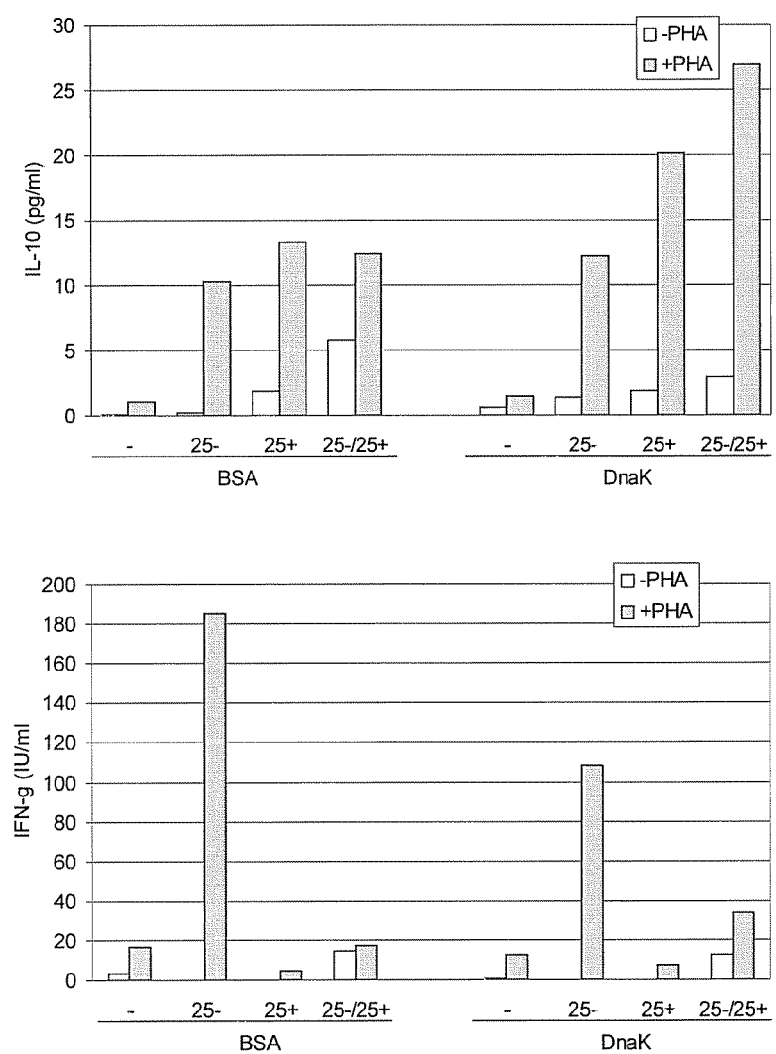

FIG. 10: IL-10 production by Treg. Purified $CD4^+/CD25^+$ cells and/or $CD4^+CD25^-$ cells were added in precise amounts to purified dendritic cells pretreated 3 days with DnaK (10 μg/ml) or BSA (10 μg/ml). Cells were further cultured in the presence of DnaK or BSA and were stimulated or not with PHA. IFN-γ and IL-10 were quantitated in the culture medium by ELISA. 25-/25+ represents the mixing of the 2 populations in a 1/1 ratio.

Figure 11:
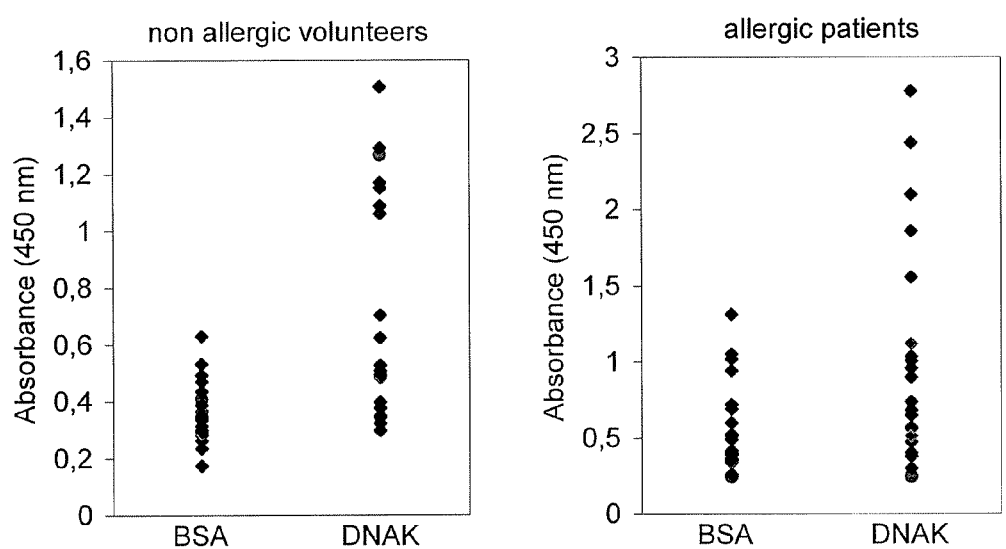

FIG. 11: Presence of anti-DnaK antibodies in human serum. DnaK or BSA were coated in 96 well plates to be used as capture protein for the ELISA test. Serum from healthy volunteers and allergic patients were used at a dilution of 1/100. IgG were detected with anti-human IgG-HRP antibodies.

The invention is explained in more details by the following examples.

EXAMPLES

Example 1

DnaK Production and Purification

DnaK Production
Bacterial strain

The *Escherichia coil* strain JS219/pOFXtac-1/KJ1 is genetically modified by the introduction of a plasmid coding for the *E. coil* DnaK. Cloning step and the construction of the vector pOFXtac-1/KJ1 have been described by Castanie M P, Berges H, Oreglia J, Prere M F, Fayet O A set of pBR322-compatible plasmids allowing the testing of chaperone-assisted folding of proteins overexpressed in *Escherichia coil;* Anal Biochem (1997) 254(1): 150-152.

Pre-Culture

One vial of Master Seed (1.5 ml) is allowed to thaw to room temperature. Three 2 l shake flasks containing 500 ml of YES+kanamycin medium (30 g/l yeast extract, 5 g/l NaCl and 50 mg/l kanamycin acid sulfate) are each inoculated with 400 μl of Master seed and incubated under shaking (270 rpm) for 6±0.5 hours at 37° C., until the $OD_{600\,nm}$ is above 0.7 units Fermentation The volume of pre-culture is added to a pre-sterilised fermentor containing 50 l of NRJ18 +kanamycin medium ($KH_2PO_4$ 5.2 g/l, $K_2HPO_4$ 10.7 g/l, glycerol 0.4 g/l, yeast extract 50 g/l, soya peptone 30 g/l, $MgSO_4$*$7H_2O$ 2.5 g/l, SAG471 0.6 ml/l, kanamycin acid sulfate 100 mg/l). The temperature is maintained at 37° C.±5° C. and the pressure at 360 mbar. When optical density is 25 ±1, the culture is induced by addition of IPTG (1 mM final concentration). The induction conditions are then maintained for 4 hours. The culture is rapidly cooled below 20° C. The medium is filtered trough a 50 pm Sartopure PP2 filtration device. The cell pellets were recovered by centrifugation at 4500 rpm (5000× g) for 30 minutes at 4° C. and frozen at −20° C. until use.

Cell Disruption and Supernatant Filtration

The cell pellets are thawed at room temperature, in 20 mM Tris-HCl pH 8. Then, the cell paste concentration is adjusted at 166.6 g fresh cell weight/liter by adding buffer. The cell suspension is filled into a tank placed on ice. The homogenised cells are disrupted with a Niro Soavi Panda high-pressure disrupter at an average pressure of 800 & 50 bars, during 2 cycles.

The cell lysate is centrifuged for 30 minutes at 16000 g (8000 rpm), at 4° C. The supernatant is collected and filtered through a Sartobran P Maxicap 10 inches (0.2 μm). The filtered supernatant is kept at 4° C. overnight before next step.

DnaK Purification

Sepharose HP Chromatography (QHP)

Anion exchange chromatography is conducted with Q Sepharose HP (Amersham Biosciences). The column is packed in highly purified water at a linear flow rate of 68 cm/h (33.4 l/h). The dimensions of the packed column bed are: diameter=250 mm, cross-sectional area=132 cm$^2$, bed=25.0 cm, packed volume=approximately 12.27 l.

The filtered supernatant is diluted twice with 20 mM Tris-HCl pH 8.0 and, if required, the pH is adjusted to pH 8±0.0.1 with a 1 M Tris solution (unadjusted pH solution). Final conductivity must be <10 mS/cm. The diluted supernatant is then loaded on the column at a flow rate of 22.1 l/h (45 cm/h). After loading is complete, the column is washed with 2.0 to 3.0 CV of 20 mM Tris-HCL pH 8.0 at 19.6 l/h (41.5 cm/h), until the baseline reaches zero. The elution is performed in 2 steps at 22.1 l/h (45 cm/h): the first step is performed with 2-3 CV of 20 mM Tris-HCl+0.25 M NaCl pH 8.0 buffer. The second step is performed with 2-3 CV of 20 mM Tris-HCl+0.45 M NaCl pH 8.0 buffer. The fraction collected during this step is retained for the following purification step. The absorbance is followed at 280 nm. The eluate is stored at 2-8° C. overnight until the next purification step.

The samples (20 μl of each fraction) were denatured and loaded on a 4 to 12% Bis/Tris NU-PAGE gel. After electrophoresis, the proteins were stained with Coomassie Blue (see FIG. 1).

Hydroxyapatite Type II Chromatography (HA)

The second chromatography is conducted with Hydroxyapatite type II –40 μm (Bio-Rad). The resin (2000 g) is poured in 3.2 l of $Na_2PO_4*12H_2O+NaH_2PO_4*2H_2O$ 200 mM–pH 6.8 under gentle mixing. The column is packed with $Na_2PO_4*12H_2O+NaH_2PO_4*2H_2O$ 200 mM–pH 6.8 at a linear flow rate of 175 cm/h (26.9 l/h). The dimensions of the packed column bed are: diameter=14 cm, cross-sectional area=154 cm$^2$, bed=21.5 cm, packed volume=3.31 l.

The QHP eluate is loaded in 6 equal fractions on the HA column. All the Hydroxyapatite process is performed at a flow rate of 150 cm/h (23.1 l/h).

The column is equilibrated with 2.5 to 3.5 CV of 200 mM $NaH_2PO_4/Na_2HPO_4$ pH 6.8 followed by 2.5 to 3.5 CV of 5 mM $NaH_2PO_4/Na_2HPO_4$ pH 6.8 until pH and conductivity are stabilized.

After pH adjustment to 6.8±0.1 with 50% HCl, the QHP eluate (a sixth of the total volume) is loaded on the column (it's important to notice that the NaCl concentration of the previous chromatographic step is not important for HA adsorption). After loading is complete, the column is washed with 1.5 to 2.5 CV of 5 mM $NaH_2PO_4+Na_2HPO_4$ pH 6.8 buffer, until U.V. returns to the baseline. The absorbance is followed at 280 nm.

After that, the elution is performed with a gradient from 0% to 100% of 200 mM $NaH_2PO_4/Na_2HPO_4$ pH 6.8 buffer in 10 CV. Usually, the elution is complete after about 6 CV.

The eluted peak is collected, the pool of fractions is filtered through a 0.22 μm filter and kept at 2-8° C.

After elution, a regeneration step is performed with 2.5 to 3.5 CV of 5 mM $NaH_2PO_4+Na_2HPO_4$ pH 6.8 buffer, before the loading of the next sample.

The samples were denatured and loaded on a 4 to 12% Bis/Tris NU-PAGE gel. After electrophoresis, the proteins were stained with Coomassie Blue (see FIG. 2).

Diafiltration/Size Exclusion Chromatography

It was tried to separate the impurities by diafiltration on a 30 kDa membrane and by chromatography on a Sephacryl S100 HR resin. The impurities could not be removed by these two methods. Indeed, the impurity is recovered in the retentate of the diafiltration as DnaK. The impurity was co-eluted with DnaK in the Sephacryl S100 chromatography.

The SDS-PAGE analysis of these different samples is shown in FIG. 3. The samples were denatured and loaded on a 4 to 12% Bis/Tris NU-PAGE gel. After electrophoresis the proteins were stained with Coomassie Blue.

Gelatin Sepharose Fast Flow Chromatography (GSFF)

The third method tested to separate impurities from DnaK involves chromatography on Gelatin Sepharose Fast Flow resin (GE Healthcare). The column is packed in highly purified water at a linear flow rate of 150 cm/h (19.9 l/h). The dimensions of the packed column bed are: diameter=13 cm, cross-sectional area=133 cm$^2$, bed=15 cm, packed volume=1.99 l.

The pool of HA eluates is loaded in 9 equal fractions on the GSFF column. In between the GSFF cycles, a cleaning with 6 M Guanidium chloride is performed. All the Gelatin Sepharose process is performed at a flow rate of 120 cm/h (15.9 l/h).

The column is sanitized with 1.5 to 2.5 CV of 70% ethanol+0.1 M acetic acid with a contact time of 1 hour. It is then equilibrated with 2.5 to 3.5 CV of 0.5 M NaCl+5 mM HEPES, pH 7.5.

The HA pool of eluates (a ninth of the total volume) is loaded on the column. After loading is complete, the column is washed with 1.5 to 2.5 CV of 0.5 M NaCl+5 mM HEPES, pH 7.5 buffer, until U.V. returns to the baseline. The absorbance is followed at 280 nm.

After that, the elution is performed with 3 to 4 CV of 0.5 M NaCl +5 mM HEPES+3 mM ATP+1 mM $MgCl_2$, pH 7.5.

When the absorbance rises, fractions are collected during 2 CV. After the ninth GSFF cycle, the column is cleaned with 1.5 to 2.5 CV of 6 M Guanidium chloride then washed with 3 CV of 0.5 M NaCl+5 mM HEPES, pH 7.5 buffer and stored in 20% ethanol.

As shown in FIG. 4 chromatography on Gelatin Sepharose resin clearly improves the purity of the DnaK in comparison to the sample obtained after hydroxyapatite chromatography (comparison of lane 2 and lane 3). In this case, the purity of the DnaK is greater than 98.25% (see example 2 and FIG. 5).

When the supernatant of cell lysate is directly loaded on a Gelatin Sepharose column, the purity of the DnaK after this step is about 95%.

When the Gelatin Sepharose step is performed after the Q Sepharose HP, the purity of DnaK preparation is not increased in comparison to the sample obtained after Q Sepharose HP and Hydroxyapatite chromatography (FIG. 4 comparison of lane 2 and lane 4).

These results demonstrate that the combination of these three types of chromatography (IEX, HA and GSFF) is absolutely necessary to obtain a DnaK preparation with purity > than 98%.

Concentration and Diafiltration by Tangential Flow Filtration

Concentration is conducted with two PLCTK pellicon 2 membranes (30 kDa molecular weight cut-off, 0.1 m², Millipore,) using a Proflux M 12 (Millipore).

The membranes are washed twice with 3 l of water for injection and membranes integrity is tested prior to operation. Sanitization is performed by continuous recirculation of 0.5 M NaOH for 60 minutes. The membranes are then rinsed with $Na_2HPO_4*12H_2O$ 30 mM+$NaH_2PO_4*2H_2O$ 20 mM pH 7.3 buffer until the permeate pH reaches 7.3±0.1.

The pooled Gelatin Sepharose eluates (GSFF-E pool) are concentrated to 2000 ml and then diafiltrated against 10 volumes of $Na_2HPO_4*12H_2O$ 30 mM+$NaH_2PO_4*2H_2O$ 20 mM pH 7.3 buffer in order to exchange the buffer. The following process parameters are used: $P_{in}$=1.5±0.1 bar, $P_{out}$=0.5±0.1 bar, TMP=1 bar.

Following the diafiltration, the system and membranes are rinsed twice with 200 ml of $Na_2HPO_4*12H_2O$ 30 mM +$NaH_2PO_4*2H_2O$ 20 mM pH 7.3 buffer. The used rinsing solution is added to the diafiltrated retentate.

Following diafiltration, the system and membranes are rinsed with water for injection. Sanitization is performed by continuous recirculation with sodium hydroxide 0.5 M for 60 minutes. The system is stored in 0.1 M sodium hydroxide.

Sterile Filtration

According to a UV assay performed on the diafiltrated retentate, its concentration is adjusted to 2.5 mg/ml with $Na_2HPO_4*12H_2O$ 30 mM+$NaH_2PO_4*2H_2O$ 20 mM pH 7.3 buffer.

Filtration of the diafiltrated DnaK-ATP fraction from step 4 is performed on a Millipak 60 (0.22 µm filter). Prior to filtration, the filter is rinsed with $Na_2HPO_4*12H_2O$ 30 mM+$NaH_2PO_4*2H_2O$ 20 mM pH 7.3 buffer. All aliquots of DnaK-ATP are stored at −20° C.

Example 2

DnaK Characteristics

The DnaK obtained by example 1 is very pure:
Protein Purity
   in terms of proteins, the purity is greater than 98.25% as determined by Coomassie staining of the SDS-PAGE gel (FIG. 5). The substance was denaturated and decreasing quantitites were loaded on a 4-12% Bis/Tris NU-PAGE gel. The proteins were separated by electrophoresis, and stained with Coomassie blue R250 (0.1%). The product purity is assessed by means of comparing the intensity of each possible contaminating bands detectable in lane 2 with the band intensity of the DnaK at different dilutions.
Residual DNA Content
   the residual DNA content, quantified by RT-PCR with bacterial DNA specific primers for 23 S chromosonic DNA, is 0.22 ng/mg of protein. The quantitative real-time PCR is based on the amplification of genomic DNA by the polymerase chain reaction (PCR) method in which the amount of amplified DNA is followed in real time by fluorescence measurement, using the SYBR green dye which binds to newly formed double strand DNA. The primers for bacterial DNA have been chosen in the 23S chromosomic DNA as proposed by Smith et al. (Smith et al., BioTechnique (1999) 26: 518-526).
Residual Host Cell Protein Content
   the residual host cell protein content determined by ELISA is 0.00004%. The bacterial protein content measurement developed by Cygnus Technologies Inc. is based on the principle of sandwish ELISA. Briefly, 96 well plates are coated with capture anti-*E. coli* antibodies. *E. coli* proteins contained in the samples are trapped by these antibodies and detected using other specific *E. coli* antibodies coupled to alkaline phosphatase. After washing to remove unbound reagents, the substrate of the enzyme (p-nitrophenylphosphate—pNPP) is added and the absorbance measurement is proportional to the reaction product concentration and thus to the host cell proteins present in the sample.
Endotoxin Content
   the endotoxin content (determined by LAL method) is 0.002 E.U./µg of protein. The method used to quantify the endotoxins is the Kinetic-QCL® test developed by Cambrex. It is based on the following principle that gram negative bacterial endotoxins catalyze the activation of a proenzyme in the lysate of Limulus
   Amebocyte (LAL). Upon activation of this enzyme, p-nitroaniline (pNA-yellow) is released from Ac-Ile-Glu-Ala-Arg-pNa (colorless). The absorbance at 405 nm is measured continuously during the incubation period and is proportional to the pNA concentration in the medium. The concentration of endotoxin in the sample is calculated from its reaction time by comparison to the reaction time of known amounts of *E. coli* endotoxin standards.
Nucleotide Content
   40% of the purified DnaK obtained by this method corresponds to DnaK free of nucleotides and at the other 60% are the DnaK-ADP.

Example 3

ATPase Activity of the DnaK

In order to check the functionality of the DnaK, we have measured its ATPase activity. Exogenous ATP was added and the production ADP was followed with time. The nucleotides are analyzed by ion-pairing reverse-phase chromatography on C18 column. The rate of ATP hydrolysis is 0.05 $min^{-1}$ which is in agreement with the values reported in the literature (Jordan et McMacken, J. Biol. Chem. (1995) 270: 4563-4569). In detail, exogenous ATP (6 molar equivalents) was added to the DnaK, in the presence of Tris 50 mM, pH 7.4, $MgCl_2$ 3 mM and KCl 10 mM. An aliquot (500 µl) of the reaction medium was harvested after 5, 15, 30, 45 and 60 minutes and the reactions were stopped by adding 100 µl of HCl 1 M. Nucleotides were separated from DnaK by filtration on 10 kDa filters and after neutralisation of the filtrate, were analysed by ion-pairing reverse-phase chromatography on C18 column (FIG. 6). The elution solution was composed of 100 mM phosphate buffer and 20% methanol, tetrabutyl ammonium was used as pairing agent.

Example 4

Biological Properties of DnaK

DnaK has No Pro-Inflammatory Effect:
   When added to whole blood, DnaK induced a very low production of interleukin 1β (IL-1β), interleukin 6 (IL-6) or Tumor Necrosis Factor α (TNFα), in comparison to bacterial lipopolysaccahrides (LPS). The production of these cytokines was detectable only at high concentration of DnaK (30 µg/ml) (FIG. 7). Cytokine production was quantitated in whole blood incubated 24 h in the presence of DnaK or LPS, the measurement was performed by ELISA.

DnaK by Itself Does Not Induce TH1 or T$_H$2 Responses:

When human PBMC (peripheral blood lymphocytes) were incubated (6 days) in the presence of DnaK alone, there are no production of interferon-γ (IFN-γ) which would reflect the activation of T$_H$1 type lymphocytes (FIG. 8). The activation of T$_H$1 lymphocytes and production of IFN-γ lead to the activation of inflammation responses.

There are no production of interleukin 5 or 13 (IL-5, IL-13) (FIG. 8), which are produced following T$_H$2 lymphocyte activation. T$_H$2 responses are involved in the IgE antibodies production and mastocyte degranulation.

Positive control is PHA (phytohemagglutinin) which activate lymphocytes in a non-specific way. Cytokine production was measured by ELISA in the culture medium for 5 differents volunteers (each measurement was performed in duplicate).

A weak production of interleukin 10 (IL-10) was detectable in response to DnaK, in 2 samples from 6. IL-10 is involved in the tolerance phenomenon development.

DnaK Does Not Stimulate PBMC Proliferation:

PBMC purified from human blood were incubated in 96 well plates for 5 days in the presence of DnaK (1-9 μg/ml) or Varicella zoster virus antigen (1 CPAU/ml as positive control). 100 μl of the medium were replaced by fresh medium containing 1 μCi of tritiated thymidine and the cells were further cultured for 16 hours. On day 6, incorporation of tritiated thymidin was measured with a beta counter using liquid scintillation.

| Condition | Cpm of [$^3$H] thymidine |
|---|---|
| Buffer (negative control) | 2812 ± 3171 |
| DnaK (1 μg/ml) | 3334 ± 3441 |
| DnaK (3 μg/ml) | 3515 ± 3617 |
| DnaK (9 μg/ml) | 4405 ± 4601 |
| Varicella zoster antigens | 53408 ± 21180 |

Results are expressed as mean±standard deviation of 5 determinations.

DnaK Inhibits IFN-γ Production Induced by Another Antigen:

Human PBMC were incubated 3 days with candidin, alone or in the presence of increasing concentrations of DnaK (1-20 μg/ml). IFN-γ in the culture medium was quantitated by ELISA. Results are presented as mean±SD of 4 determinations.

Since IFN-γ is involved in the inflammation response to antigens, the fact that its production was inhibited in the presence of DnaK suggest that DnaK could have some anti-inflammatory effect (FIG. 9).

DnaK Stimulates the Production of IL-10 by Treg Cells:

IL-10 is one mediator of the tolerance. It is produced by some Treg cells, which strongly expressed CD25 on their cell surface (they are CD25$^+$ cells).

We have purified dendritic cells, CD25$^+$ and CD25$^-$ cells from human blood and mixed them in precise ratio. Dendritic cells were first incubated in the presence of BSA or DnaK (10 μg/ml), then the lymphocytes were added: CD25$^-$ alone, CD25$^+$ alone or the mixture CD25$^-$/CD25$^+$ (ratio 1:1). The culture was maintained for 3 days and the cells were stimulated or not with PHA.

As expected, the presence of CD25$^+$ cells in the culture inhibited the production of IFN-γ by CD25$^-$ cells (FIG. 10). The production of IL-10 by CD25$^+$ cells is more important for cells incubated with DnaK versus cells incubated with BSA, the production is even increased for the mixutre of cell population. This suggest that DnaK stimulates the production of IL-10 by Treg, following the activation of T cells with PHA.

There are Anti-DnaK Antibodies in Human Blood:

Using an ELISA test, we have pointed out the presence of anti-DnaK IgG in human serum. For 40% of the tested samples (from healthy volunteers and allergic patients), the OD$_{405\ nm}$ was greater in the case of DnaK than with the BSA (FIG. 11) reflecting a higher titer of IgG against DnaK than against BSA.

The invention claimed is:

1. A recombinant purified DnaK preparation comprising purified recombinant DnaK,
   the preparation
      having a purity of 98% or more;
      having an ATPase activity without the addition of any other chaperone protein; and
      essentially free of T-cell stimulating impurities.

2. The recombinant purified DnaK preparation of claim 1 having
   a) a residual DNA contamination ≤1 ng/mg of protein
   b) a residual host cell protein contamination (HCP) <5% by weight
   c) an endotoxin contamination <0.5 E.U./μg of protein.

3. The recombinant DnaK preparation of claim 1 wherein the content of peptides is below 1% on a molar basis.

4. The recombinant DnaK preparation of claim 1, wherein the residual DNA contamination is ≤0.5 ng/mg, and/or the HCP is <0.1% by weight, more preferably <0.0001% by weight.

5. The recombinant DnaK preparation of claim 1, wherein the DnaK is hydrolyzed.

6. The recombinant DnaK preparation of claim 1, wherein the endotoxin contamination is ≤0.01 E.U./μg of protein.

7. The recombinant purified DnaK preparation of claim 1, wherein the DnaK is essentially free of nucleotides, in form of a complex with ADP, in form of a complex with ATP or mixtures thereof.

8. A method for the purification of a recombinant DnaK preparation of claim 1 from a cell lysate comprising the steps of:
   a) ion exchange chromatography;
   b) hydroxylapatite chromatography; and
   c) gelatin chromatography.

9. The method of claim 8 wherein DnaK is from saprophytic bacteria, preferably E. coli.

10. The method of claim 8 wherein the ion exchange chromatography is an anion exchange chromatography.

11. The method of claim 8 wherein the hydroxylapatite chromatography is a hydroxylapatite type II chromatography.

12. The method of claim 8 wherein the gelatin chromatography is conducted on gelatin sepharose.

13. A method for forming a complex between recombinant DnaK and at least one peptide or at least one protein comprising the steps of:
   a) combining recombinant DnaK of claim 1 with ATP at molar ratio HSP:ATP of 1:1 to 1:10;
   b) adding at least one peptide or at least one protein; and
   c) incubating at a temperature of 10° C. to 60° C., preferably 20° C. to 45° C.

14. A mixture of recombinant DnaK according to claim 1 and at least one peptide or at least one protein.

15. A pharmaceutical product comprising a recombinant purified DnaK preparation of claim 1.

16. The mixture of claim 14 wherein the mixture is in the form of a complex.

17. A pharmaceutical product comprising a mixture of claim 14.

18. The recombinant purified DnaK preparation of claim 1 wherein the presence of the T-cell stimulating impurities is determined at a concentration of 1 µg of the purified recombinant DnaK per ml of blood.

19. The recombinant purified DnaK preparation of claim 1 wherein the lack of the T-cell stimulating impurities is evaluated through observation of no T-cell proliferation up to 30 µg of the purified recombinant DnaK per ml of blood and no TNF-α production up to 10 µg of the purified recombinant DnaK per ml of blood.

* * * * *